United States Patent
Müller et al.

(10) Patent No.: US 10,292,788 B2
(45) Date of Patent: May 21, 2019

(54) FILM CLAMPING ELEMENT

(71) Applicant: Ivoclar Vivadent AG, Schaan (LI)

(72) Inventors: Frank Müller, Feldkirch (AT); Lukas Enggist, Sargans (CH); Nora Christina Kögel, Oberriet (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/320,884

(22) PCT Filed: Jun. 22, 2015

(86) PCT No.: PCT/EP2015/063995
§ 371 (c)(1),
(2) Date: Dec. 21, 2016

(87) PCT Pub. No.: WO2015/197560
PCT Pub. Date: Dec. 30, 2015

(65) Prior Publication Data
US 2017/0196659 A1    Jul. 13, 2017

(30) Foreign Application Priority Data

Jun. 26, 2014  (DE) .................. 10 2014 109 023

(51) Int. Cl.
| | |
|---|---|
| A61C 5/12 | (2006.01) |
| A61C 5/82 | (2017.01) |
| A61C 5/90 | (2017.01) |
| A61B 13/00 | (2006.01) |
| A61B 1/24 | (2006.01) |

(52) U.S. Cl.
CPC .................. *A61C 5/82* (2017.02); *A61B 1/24* (2013.01); *A61B 13/00* (2013.01); *A61C 5/90* (2017.02)

(58) Field of Classification Search
CPC .. A61C 5/82; A61C 5/90; A61B 13/00; A61B 1/24
See application file for complete search history.

(56) References Cited

U.S. PATENT DOCUMENTS

| | | | | |
|---|---|---|---|---|
| 4,600,387 A | * | 7/1986 | Ross ........................ | A61C 5/82 433/136 |
| 5,340,313 A | * | 8/1994 | Hussin ..................... | A61C 5/82 433/136 |

(Continued)

FOREIGN PATENT DOCUMENTS

| | | |
|---|---|---|
| DE | 29702483 U1 | 4/1997 |
| JP | S54-056803 A | 5/1979 |

(Continued)

OTHER PUBLICATIONS https://medical-dictionary.thefreedictionary.com/frenulum+of+the+tongue, "Frenulum of the tongue," Medical Dictionary, Farlex and Partners, 2009. Retrieved on Sep. 11, 2018.

*Primary Examiner* — Nicholas D Lucchesi
(74) *Attorney, Agent, or Firm* — Ann M. Knab; Thad McMurray

(57) ABSTRACT

The invention relates to a film clamping element, in particular for carrying out dental treatment in the mouth area of a patient, comprising a vestibular ring (14) and a lip ring (12), between which and optionally beyond which a film (16) extends. The film is held in a stretched manner by the rings, and the film (16) and the rings are elastically deformable, in particular the film and the rings can be pressed together into a substantially oval shape. The invention is characterized in that the vestibular ring (14) has a recess on at least one circumferential point, the width of said recess being greater than the width of a frenulum and smaller than the radius of the vestibular ring (14).

27 Claims, 10 Drawing Sheets

(56) References Cited

U.S. PATENT DOCUMENTS

| | | | |
|---|---|---|---|
| 5,518,503 A * | 5/1996 | Rooney | A61B 13/00 600/240 |
| 5,524,644 A | 6/1996 | Crook | |
| 6,022,214 A | 2/2000 | Hirsch | |
| 7,988,626 B2 | 8/2011 | Horvath | |
| 2003/0190584 A1* | 10/2003 | Heasley | A61C 5/82 433/136 |
| 2004/0097795 A1* | 5/2004 | Horvath | A61C 5/90 600/237 |
| 2004/0209224 A1* | 10/2004 | Heasley | A61C 5/82 433/139 |
| 2006/0223028 A1* | 10/2006 | Horvath | A61C 5/82 433/136 |
| 2008/0153058 A1* | 6/2008 | Horvath | A61C 5/90 433/140 |
| 2009/0035718 A1 | 2/2009 | Coffee | |
| 2009/0053668 A1* | 2/2009 | Kim | A61C 5/82 433/29 |
| 2013/0199545 A1 | 8/2013 | Burns | |
| 2013/0344455 A1* | 12/2013 | Hull | A61C 5/125 433/29 |
| 2014/0007884 A1 | 1/2014 | Frey | |
| 2017/0333159 A1* | 11/2017 | Pietarinen | A61B 13/00 |

FOREIGN PATENT DOCUMENTS

| | | |
|---|---|---|
| JP | H11178792 A | 7/1999 |
| JP | 3083615 U | 2/2002 |

\* cited by examiner

FILM CLAMPING ELEMENT

CROSS-REFERENCE TO RELATED APPLICATIONS

This application is a National Stage application of International patent application PCT/EP2015/063995 filed on Jun. 22, 2015, which claims priority to German patent application No. 10 2014 109 023.3 filed on Jun. 26, 2014, the disclosures of which are incorporated herein by reference in their entirety.

The invention relates to a film clamping element according to the preamble of claim 1.

A film clamping element of this type has been used successfully for almost ten years in order to enable free access to the mouth of the patient in case of dental treatment in the mouth area of a patient. It consists of a vestibular ring and a lip ring between which a film extends. With this element, the film is mounted displaceably relative to both rings and elastic. It is configured without latex in order to avoid allergic reactions.

Folding over the film is to ensure that it is held automatically.

In case of maloperation, it may slide over the slightly smaller vestibular ring such that the function of the film clamping element can be omitted in this respect.

Thus, the invention is based on the task of providing an improved and easy-to-handle film clamping element according to the preamble of claim 1 which is also more mouth compatible.

This task is inventively solved by claim 1. Advantageous developments may be taken from the subclaims.

According to the invention it is particularly favorable if the film comprises a non-exactly constant shape at the vestibular ring but a recess at specific and rather narrow positions. For instance, the area of the frenulum can be recessed and the areas of the vestibular ring surrounding the frenulum can be provided with a padding. In this case, the padding can also serve to fix the film at this position which makes it possible to prevent the film from being drawn accidentally over the vestibular ring and from collapsing.

Still, by stretching the film across the—usually larger—lip ring, three-dimensional adjustability and deformability is given surprisingly easily, and the inventive preventive function is ensured reliably. The padding on the side of the frenula can be configured as a thickening of the film which is drawn over the vestibular ring and which offers a more pleasant-to-wear sensation compared to the actual vestibular ring thereat. The mouth of the patient is pushed open gently in the vestibule without the patient having the feeling of a forced mouth gag.

According to the invention, a clamping force acts purposefully against the lips which abut against the upper side and the bottom side of the film, and due to the soft padding support in the vestibule this clamping force is surprisingly considered to be barely uncomfortable by the patient. Contrary to this, the clamping force of the film in the area of the cheeks and mouth corners is substantially lower, for instance by one order of magnitude.

According to the invention, by combining these measures the wearing comfort is improved considerably compared to the solutions known up to now in this respect in spite of the use of a substantially equally elastic vestibular ring, and additionally the risk that the film slips off of the vestibular ring is eliminated.

Furthermore, the additional elasticity in the area of the padding also reduces the load on the elastic vestibular ring in terms of bend protection; in this respect, according to the invention the elasticity of the padding is greater than the elasticity of the actual vestibular ring.

In an inventively preferred embodiment the actual vestibular ring can be deformed in a bent manner radially towards the inside in the area of the frenula, that is to say at opposite positions. However, in a modified embodiment it is sufficient to configure projections to the sides of the recess areas which projections can be configured to be deformable elastically and/or plastically.

Different kinds of paddings are possible according to the invention. In this way, the physiological conditions in the mouth cavity, that is to say moisture and/or heat, can be used by means of deformability using heat or moisture in order to activate the desired deformability only when the invention is applied. It is also possible to equip the padding with a membrane which can be permeated by a liquid unilaterally in one direction and blocks the opposite direction. In this way, an absorption of a liquid is ensured which at the same time also ensures the padding of the vestibular ring, for instance, by arranging absorption elements within the membrane. These elements provide a padding for the slightly harder actual vestibular ring towards the outside.

It is also possible to configure the padding areas as hollow members and/or to make sure that they extend only at those positions which are subject to pressure. For instance, respective padding elements can extend towards the outside at a distance of about 1 cm from the central center—which corresponds to the areas of the frenula—for instance over 1 cm to 3 cm, preferably approximately 2 cm.

Then, the lateral areas of the vestibular ring are free from padding elements and, in this connection, slightly more elastic than the padding areas.

Then, the hollow members can be filled either with a liquid such as water, with air or with an absorbent material such as a sponge, and they can either be set to a desired internal pressure by actuation through the operator, or they can be preset to a predetermined internal pressure from the outset. When the hollow members are filled with a liquid, the waterbed effect can be realized by filling the respective hollow member only partially. In this case, an ideal and at the same time cooling adjustment to the contact surface in the vestibule takes place.

When the actual vestibular ring is not configured circularly, the desired restoring forces can be set by exactly determining the stiffness at different radial positions of the vestibular ring, and it is also possible to realize plastic partial deformability in addition to elastic deformability.

The vestibular ring can also be preshaped in an ovally flattened manner in a modified embodiment.

Further advantages, details and features of the invention may be taken from the following description of several exemplary embodiments of the invention in conjunction with the drawings, in which.

Figure 1:
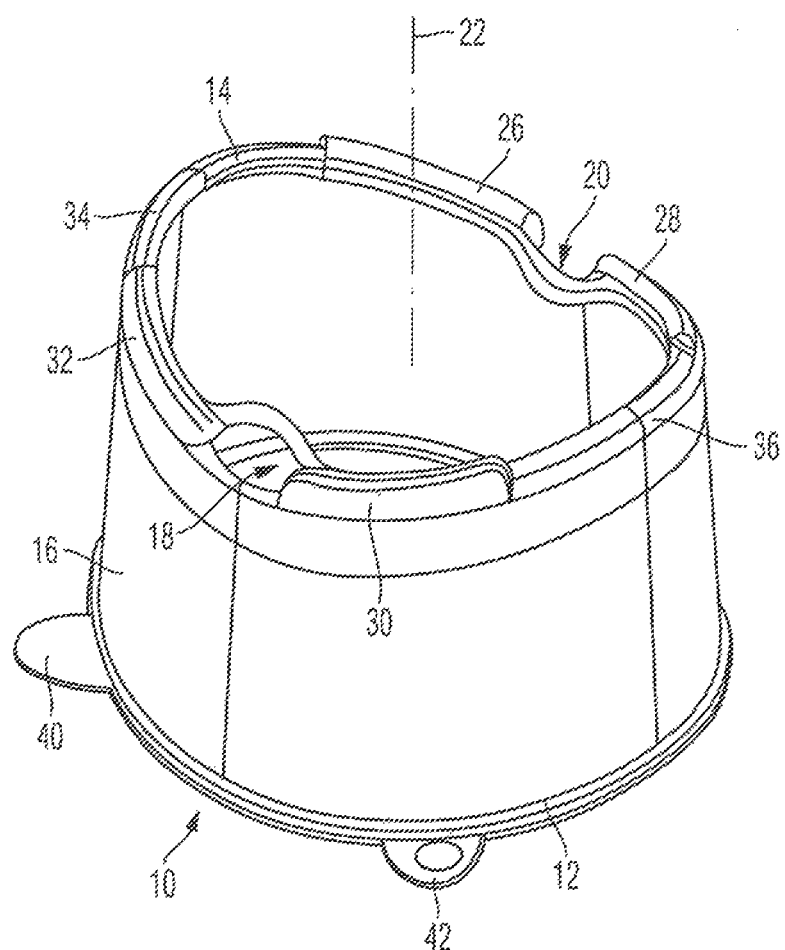
FIG. 1 shows a perspective view of an embodiment of a film clamping element.

The film clamping element 10 according to FIG. 1 comprises a lip ring 12 and a vestibular ring 14. A film 16 is positioned between them which is attached to both the vestibular ring 14 and the lip ring 12 in the exemplary embodiment illustrated in FIG. 1.

In a modified embodiment, the film 16 is mounted firmly on the vestibular ring 14, however, folded over the lip ring 12 in a way known per se such that three-dimensional displaceability and deformability exist in this connection.

FIG. 1 shows that the shape of the lip ring 12 and the shape of the vestibular ring 14 deviate from a circular shape considerably and are deformed ovally/triangularly relative to it. In both cases, the shape is a closed ring shape.

In this embodiment, the film 16 is basically non-rigid. If no tensile force was applied between the vestibular ring 14 and the lip ring 12, it would collapse as a result.

In a further preferred embodiment, a type of soft support corset can be provided which is incorporated in the film 16 and which keeps the rings 12 and 14 at a distance, and keeps the film 16 stretched in the target shape, respectively. This support corset is configured so softly that upon pressure exerted by the lips on the film the latter deforms easily and without considerable resistance in a lip-friendly manner and thus moves the vestibular ring 14 and the lip ring 12 slightly towards one another by deforming the film 16, or keeps the film in the target shape already.

According to the invention, the vestibular ring 14 is configured in a particular manner. It comprises two recesses 18 and 20. They are opposite one another and are intended for being inserted into the vestibule in the positions at which the frenula extend. There, the vestibular ring 14 extends towards an axis 22 of the film clamping element 10 in a curved manner such that the hard part of the vestibular ring 14 is prevented from coming into contact with the frenula. Accordingly, the dimension of the recess amounts to at least several millimeters, for instance 5 mm.

In this connection, in order to strengthen the effect of the recess and to improve the wearing comfort projections 26, 28, 30 and 32 are provided on the sides of the recesses 18 and 20. These projections 26 to 30 serve as a padding of the vestibular ring 14. They are made of a softer material than the actual vestibular ring 14 and surround it at least in the radial direction to the outside and in a direction parallel to the axis, with regard to the axis 22. This is apparent from FIG. 1.

The projections 26 to 32 serve as a padding and also project significantly relative to the actual vestibular ring, for instance by 3 mm.

They extend over a few centimeters on the side of the recess area 18 and 20, however, they leave blank the lateral areas 34, 36 such that they can bend elastically in an unimpeded manner.

Thus, the spring resistance of the vestibular ring 14 is lowest in the lateral areas 34 and 36 and higher than in the lateral area both in the area of the paddings 26 to 32 and in the area of the recesses 18 and 20.

The elliptical or slightly triangular shape of the vestibular ring 14 in the strain-free state enables a soft and elastic deformation upon insertion of the vestibular ring 14 into the vestibule. The paddings 26 to 32 increase the wearing comfort considerably, and even if the patient works on the respective area with his/her tongue due to the insertion of a foreign object into his/her mouth, the film 16 is not separated from the vestibular ring 14.

The lip ring 12 is provided with orientation projections 40 and 42. They are to be allocated to the upper jaw of the patient, and can be provided, for instance, with identification or manufacturers signs. They extend transverse to the axis 22 of the lip ring 12 towards the outside and are provided in the embodiments in which the film 16 is not folded over the lip ring 12 and moveable relative to it, but fixed to it.

Figure 2:
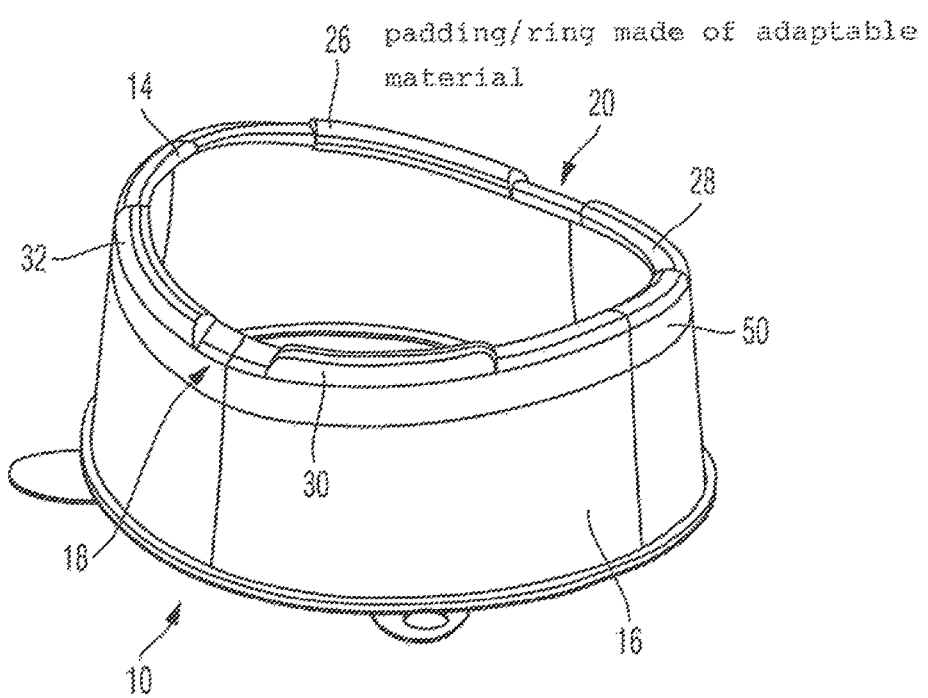
FIG. 2 shows a further embodiment of an inventive film clamping element, also in a perspective view.

A further embodiment of the inventive film clamping element 10 is apparent from FIG. 2. Here, an integrated vestibular ring 14 made of a uniform material extends, into which the desired profiling is incorporated. The material used thereat is soft and surrounds the hard component of the vestibular ring 14 completely. This entire padding 50 avoids contact between hard materials of the vestibular ring 14 and the vestibule of the patient on the other hand, however, it enables the realization of recesses 18 and 20 and projections 26 to 32. The padding material of the padding 50 can be attached in any suitable manner by moulding onto the vestibular ring 14 or the film 16.

Figure 3:
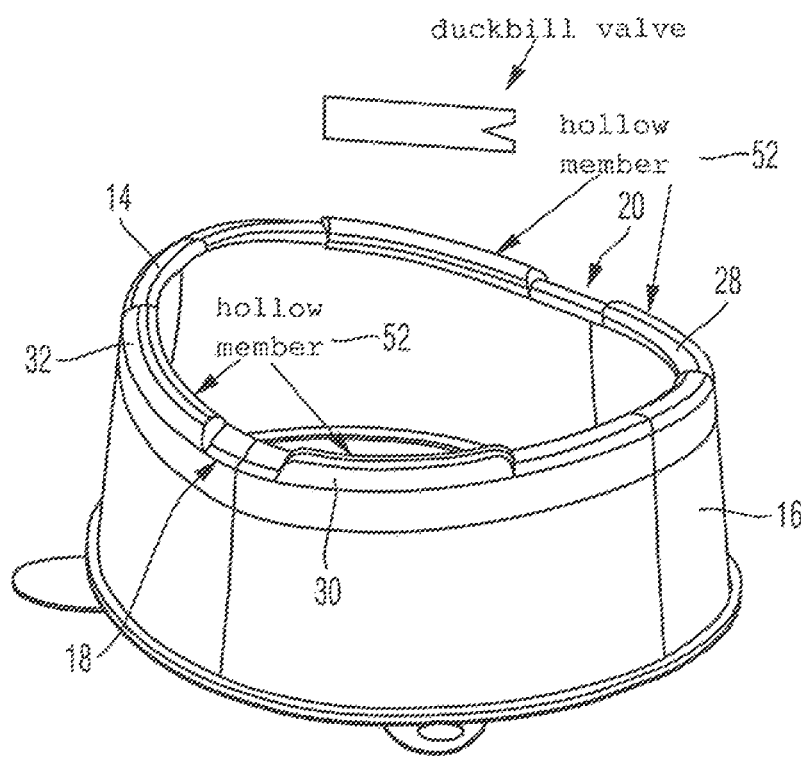
FIG. 3 shows a third embodiment of an inventive film clamping element in a perspective view.

In the embodiment according to FIG. 3 hollow members 52 are provided as paddings 26 to 32. The hollow members 52 are inflatable in this exemplary embodiment, for instance by means of a small manually operated pump comprising a duckbill valve. This further increases the wearing comfort of the vestibular ring 14.

Figure 4:
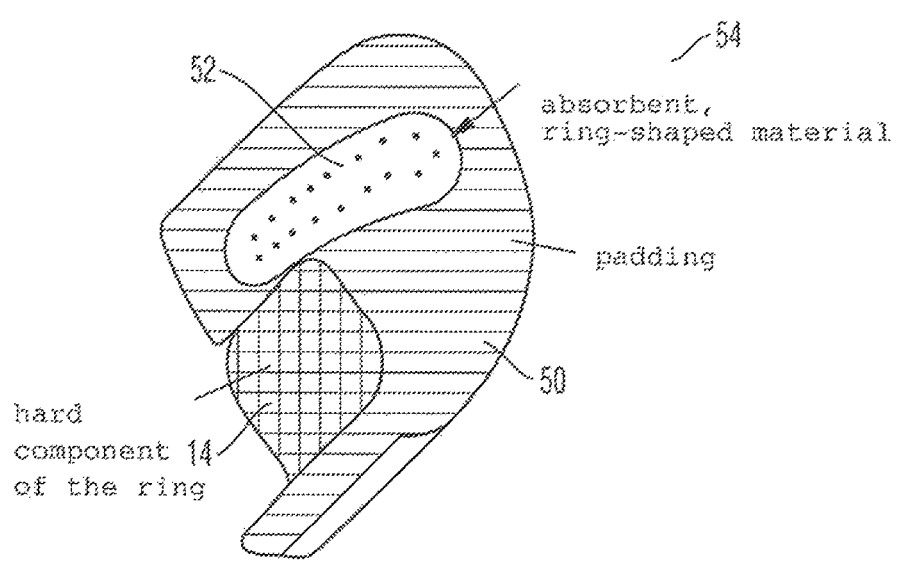
FIG. 4 shows a view of a detail of an inventive film clamping element according to a further embodiment.

FIG. 4 illustrates how a hollow member 52 can also be formed at the vestibular ring 14. The vestibular ring 14 is surrounded by the padding material 50 on three sides. It surrounds a cavity 52, in turn.

In the exemplary embodiment illustrated, the cavity 52 is filled with absorbent material, for instance a sponge. When a liquid is supplied, which can also take place in the mouth of the patient automatically, the absorbent material 54 swells and thus increases the padding effect towards the vestibular ring 14.

Figure 5:
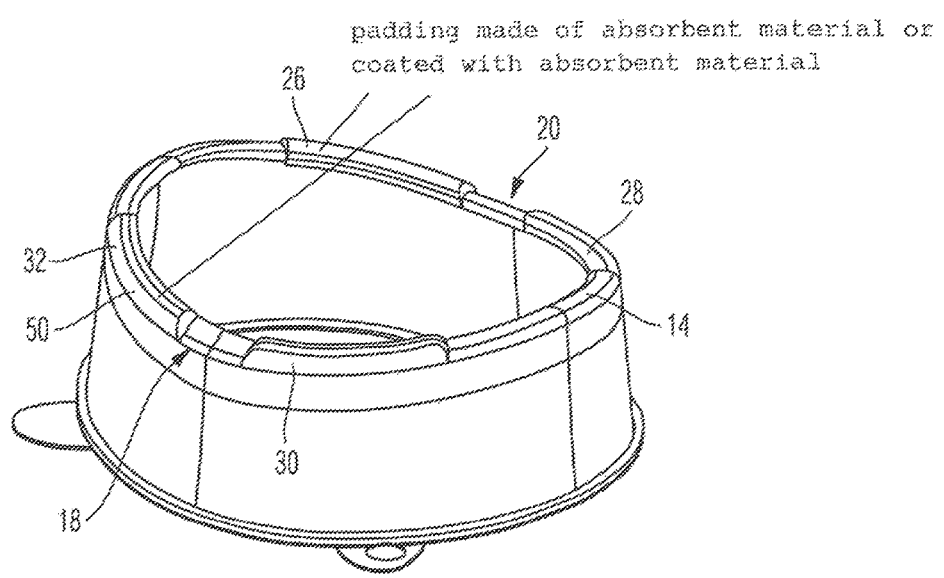
FIG. 5 shows a perspective view of a further embodiment of an inventive film clamping element.

In the embodiment according to FIG. 5 the vestibular ring 14 is coated with absorbent material at the four positions 26 to 32 which are spaced apart laterally from the recesses 18 and 20 and adjacent to them. When said material comes into contact with a liquid, it automatically increases its volume and in addition adjusts to the surroundings, that is to say the vestibule, in a smoothly resilient manner.

Figure 6:
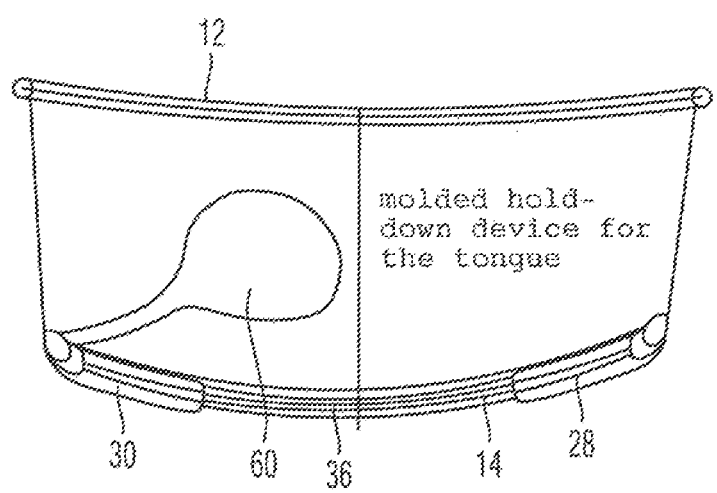
FIG. 6 shows a further embodiment of an inventive film clamping element, but in a schematic side view.

In the embodiment according to FIG. 6, it is provided to mold a hold-down device 60 to the vestibular ring 14. This device makes possible to fix the tongue of the patient during the treatment and to keep it away from the work area.

Here, and also in the other Figures, the same reference numerals refer to the same or corresponding parts such that an additional explanation can be omitted.

Figure 7:
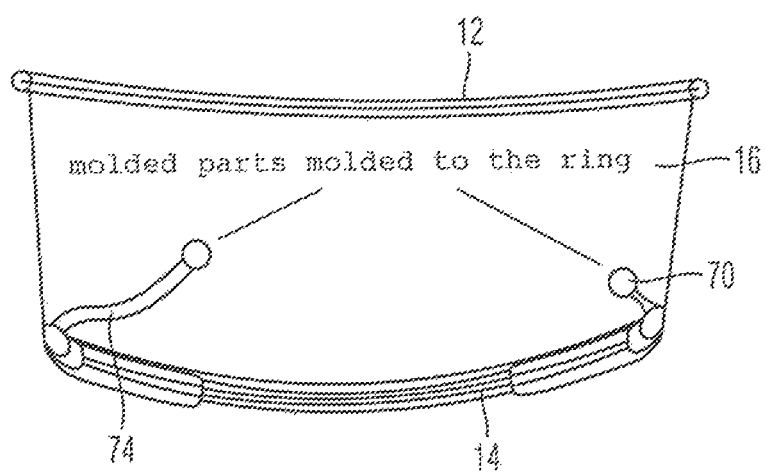
FIG. 7 shows a side view of a further embodiment of an inventive film clamping element.

In the embodiment according to FIG. 7, play elements 74 and 76 are attached to the vestibular ring 14. They encourage the tongue to play with them such that the tongue is automatically kept away from the treatment spot in a playful manner.

Figure 8:
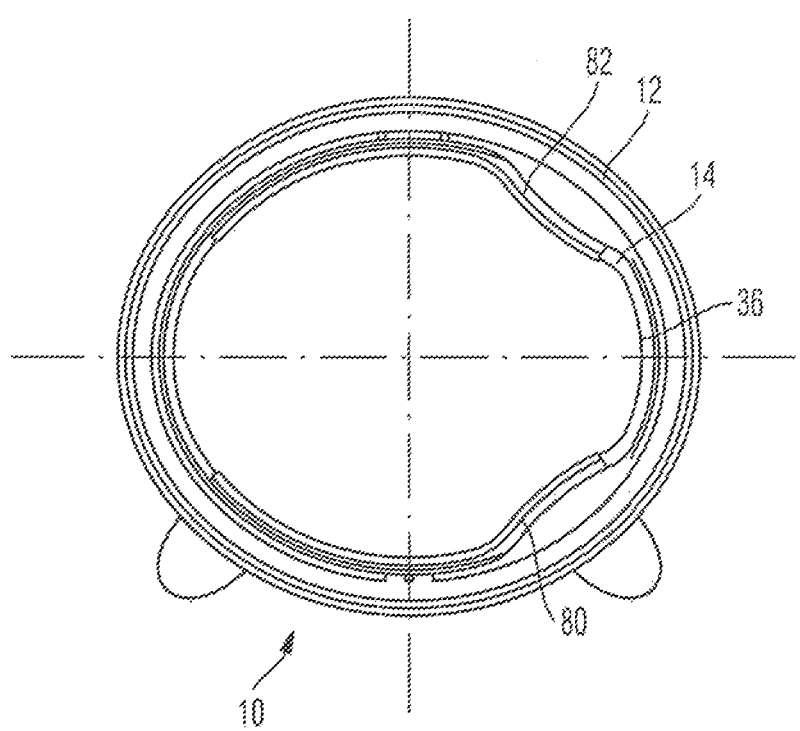
FIG. 8 shows a plan view of a further embodiment of an inventive film clamping element.

As is apparent from FIG. 8, it is also possible to realize the vestibular ring 14 asymmetrically in this configuration. If, for instance, certain areas of the mouth or the lips require a smaller opening, a relaxation of the patient can be obtained by making the vestibular ring 14 thereat recede further in the radial direction. Then, a lengthily opening of the patient's mouth is considered less unpleasant, contributing further to compliance and patient comfort of the inventive film clamping element 10.

For this purpose, the vestibular ring comprises inward bulgings 80 and 82 in which it is bent slightly radially towards the inside in the area of the paddings, that is to say spaced apart from the lateral area 36.

Figure 9:
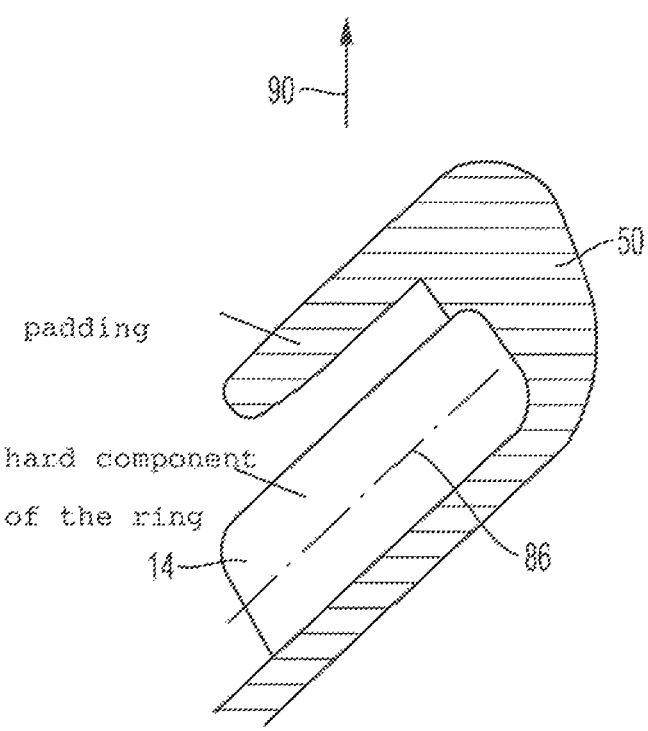
FIG. 9 shows a sectional view of a detail of a further embodiment of an inventive film clamping element.

FIG. 9 illustrates that the vestibular ring 14 can also be configured with a non-circular cross-section, for instance in a tape-shaped manner. In the exemplary embodiment illustrated the extension axis 86 of the vestibular tape extends obliquely towards the outside, and the cross-section of the vestibular ring 14 is substantially rectangular with rounded off corners.

Instead, it can also be trapezoidal, wherein it is always important that the padding 50 surrounds the hard component 14 of the ring with a large volume particularly radially towards the outside (arrow 90).

Figure 10:
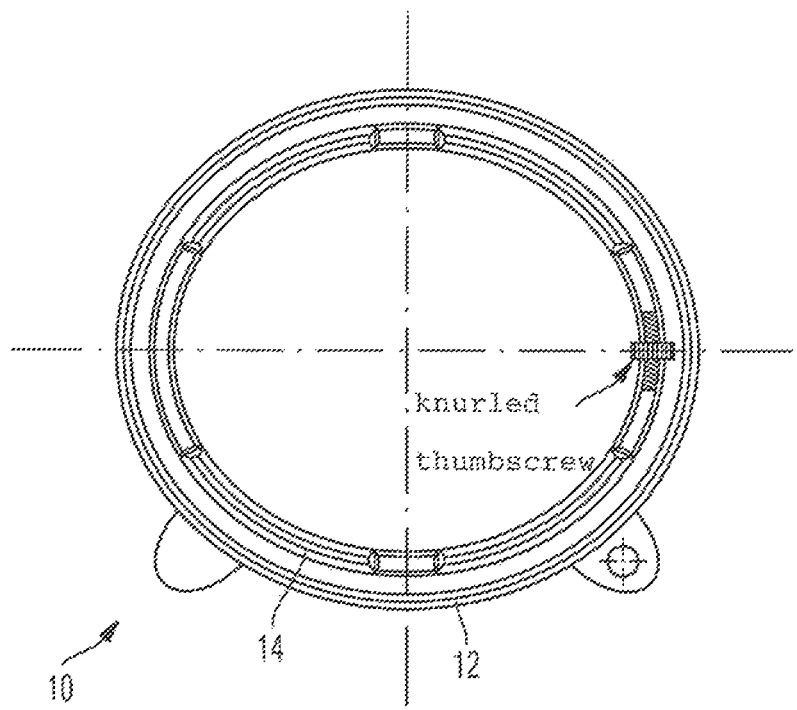
FIG. 10 shows a plan view of a further embodiment of an inventive film clamping element.

According to a further embodiment, it is provided to configure the length of the vestibular ring 14 so as to be adjustable. In this way, it is possible to cover numerous different patient sizes with the same film clamping element 10, for instance also children. The adjustability can be realized in any suitable manner, wherein a knurled thumb-screw is provided in FIG. 10 by way of example.

Instead, the ring shape of the vestibular ring 14 can also have an overlapping area, and the ends of the vestibular ring can be mounted such that they are displaceable relative to one another, but fixable.

It is also possible to provide the vestibular ring at one end thereof with a snap and on the other end thereof with a snap-in tongue which face one another in order to set the length in any suitable manner, but fixable. Here, fixation can also take place only by frictional contact optionally, instead of by positive engagement.

The invention claimed is:

1. A film clamping element, for carrying out dental treatment in the mouth area of a patient, comprising a vestibular ring (14) and a lip ring (12), between which and beyond which a film (16) extends, which film is held in a stretched manner by the rings, wherein the film (16) and the rings are elastically deformable by the application of forces between an upper side of the film clamping element and a bottom side of the film clamping element, wherein the vestibular ring (14) can be pressed together into a substantially oval shape by pressing together an upper side and an opposite bottom side thereof, wherein
   the vestibular ring (14) comprises a recess on at least one circumferential point, on the upper side and/or the bottom side, the width of said recess being greater than the width of a frenulum and smaller than the radius of the vestibular ring (14), and
   a pre-loading corset or lip support corset for the film (16) extends at least partially between the vestibular ring (14) and the lip ring (12) which brings the shape of the film (16) closer to a target shape in the inserted state.

2. The film clamping element as claimed in claim 1, wherein the recess is configured with a width of 0.5 cm to 3 cm.

3. The film clamping element as claimed in claim 1, wherein the vestibular ring (14) comprises a padded projection (26, 28, 30, 32) in an area subsequent to the recess, and wherein forces producing the oval shape substantially act between recesses (18, 20) which are arranged opposite one another and the projections (26, 28, 30, 32) and press the recesses towards each other.

4. The film clamping element as claimed in claim 1, wherein the vestibular ring (14) comprises plastically deformable material which is elastic at room temperature and at least also plastically deformable at 37° C.

5. The film clamping element as claimed in claim 1, wherein the vestibular ring (14) is deformable exclusively elastically or almost exclusively elastically in the dry state, and also plastically deformable in the moist state.

6. The film clamping element as claimed in claim 1, wherein the vestibular ring (14) comprises a material which is swellable in the moist state.

7. The film clamping element as claimed in claim 1, wherein the vestibular ring (14) comprises a cover with a membrane which is permeable to moisture, and wherein within the membrane in the area of the vestibular ring (14) moisture-absorption elements are arranged.

8. The film clamping element as claimed in claim 1, wherein the vestibular ring (14) comprises at least one material polymerizable by light and/or heat.

9. The film clamping element as claimed in claim 1, wherein the vestibular ring (14) is deformable reversibly, and partially resilient elastically in case of plastic deformation.

10. The film clamping element as claimed in claim 1, wherein the vestibular ring (14) comprises at least one hollow member (52) which can be filled with air, via a valve and a manually operated pump.

11. The film clamping element as claimed in claim 1, wherein the vestibular ring (14) can be filled with a liquid.

12. The film clamping element as claimed in claim 11, wherein the liquid comprises water, and comprises a flexible hollow member (52).

13. The film clamping element as claimed in claim 1, wherein the vestibular ring (14) comprises a padding which comprises an absorbent material which is swellable when the absorbant material absorbs a liquid.

14. The film clamping element as claimed in claim 1, wherein the vestibular ring (14) comprises a padding with a foam or other flexible material.

15. The film clamping element as claimed in claim 1, wherein the vestibular ring (14) comprises a padding which is covered by a membrane through which a liquid can pass from the outside to the inside and which blocks the passage of a liquid from the inside to the outside.

16. The film clamping element as claimed in claim 1, wherein a tongue hold-down device is molded to the vestibular ring (14) which extends away from the vestibular ring (14) starting from the film clamping element (10).

17. The film clamping element as claimed in claim 1, wherein play elements for the tongue of the patient are attached radially inwardly at the film (16) or at the vestibular ring (14) or the lip ring (12), said play elements intended for the sensory attraction of the tongue.

18. The film clamping element as claimed in claim 1, wherein the rings comprise at least one flattening or an arc at at least one predetermined position asymmetrically, to increase or decrease the clamping force acting radially towards the outside.

19. The film clamping element as claimed in claim 18, wherein the rings are deformable in the shape of an oval.

20. The film clamping element as claimed in claim 1, wherein the vestibular ring (14) is configured to have a non-circular cross-section and comprises a substantially rectangular or trapezoidal cross-section with rounded off corners which is sloped relative to the axis of the ring and which is padded at least radially towards the outside.

21. The film clamping element as claimed in claim 1, wherein a thickening of the film (16) is configured as a padding of the vestibular ring (14).

22. The film clamping element as claimed in claim 1, wherein the film (16) is held non-displaceably relative to the vestibular ring (14) and surrounds at least half of it.

23. The film clamping element as claimed in claim 22, wherein the film (16) surrounds approximately three quarters or the entire vestibular ring.

24. The film clamping element as claimed in claim 1, wherein the vestibular ring (14) is configured as a ribbon with a non-circular cross section and wherein the longitudinal axis of the ribbon extends at an angle of 45° or less to the axis (22) of the vestibular ring (14), and wherein the ribbon is surrounded by a padding which comprises softer material than the vestibular ring (14).

25. The film clamping element as claimed in claim 1, wherein the vestibular ring (14) and the lip ring (12) comprise an adjustment device by means of which the length thereof, and the size of a through-hole stretched by the adjustment device, is adaptable to be changed.

26. The film clamping element as claimed in claim 1, wherein the one recess has a width of approximately 1 cm.

27. The film clamping element as claimed in claim 1, wherein at least two recesses (18 and 20) are configured which are arranged opposite each other at a circumference and which have a width of 0.5 cm to 3 cm.

* * * * *